(12) United States Patent
Gehring et al.

(10) Patent No.: US 6,897,315 B2
(45) Date of Patent: May 24, 2005

(54) METHOD FOR PRODUCING 8-METHOXY-QUINOLINECARBOXYLIC ACIDS

(75) Inventors: Reinhold Gehring, Wuppertal (DE); Klaus Mohrs, Wuppertal (DE); Werner Heilmann, Wuppertal (DE); Herbert Diehl, Leverkusen (DE)

(73) Assignee: Bayer HealthCare Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/406,129

(22) Filed: Apr. 3, 2003

(65) Prior Publication Data

US 2003/0208069 A1 Nov. 6, 2003

Related U.S. Application Data

(63) Continuation of application No. 09/554,985, filed as application No. PCT/EP98/07237 on Nov. 12, 1998, now abandoned.

(30) Foreign Application Priority Data

Nov. 24, 1997 (DE) .......................... 197 51 948
Sep. 19, 2000 (DE) .......................... 100 46 267

(51) Int. Cl.[7] .......................... C07D 471/04
(52) U.S. Cl. .................. 546/113; 546/156; 544/105; 544/363
(58) Field of Search ............... 544/105, 363; 546/113, 156

(56) References Cited

U.S. PATENT DOCUMENTS

| | | | |
|---|---|---|---|
| 4,990,517 A | 2/1991 | Petersen et al. | 514/300 |
| 5,051,509 A | 9/1991 | Nagano et al. | 546/156 |
| 5,059,597 A | 10/1991 | Petersen et al. | 514/224.5 |
| 5,395,944 A | 3/1995 | Petersen et al. | 548/453 |
| 5,416,096 A | 5/1995 | Petersen et al. | 514/312 |
| 5,480,879 A | 1/1996 | Petersen et al. | 514/202 |
| 5,556,979 A | 9/1996 | Philipps et al. | 546/123 |
| 5,574,161 A | 11/1996 | Petersen et al. | 546/167 |
| 5,607,942 A | 3/1997 | Petersen et al. | 546/200 |
| 5,621,105 A | 4/1997 | Petersen et al. | 546/167 |
| 5,679,689 A | 10/1997 | Petersen et al. | 514/312 |
| 5,739,339 A | 4/1998 | Philipps et al. | 546/158 |
| 5,849,752 A | 12/1998 | Grunenberg et al. | 514/300 |
| 6,018,054 A | 1/2000 | Philipps et al. | 548/430 |

FOREIGN PATENT DOCUMENTS

| | | | |
|---|---|---|---|
| CA | 2005015 | 6/1990 | |
| CA | 2086914 | 7/1993 | C07D/471/04 |
| CA | 2108060 | 4/1994 | |
| DE | 4234330 | 4/1994 | |
| DE | 19546249 | 6/1997 | |
| EP | 0106489 | 4/1984 | |
| EP | 0230295 | 7/1987 | |
| EP | 0235762 | 9/1987 | |
| EP | 0241206 | 10/1987 | |
| EP | 0342675 | 11/1989 | |
| EP | 0357047 | 7/1990 | |
| EP | 05500903 | 7/1993 | |
| EP | 0591808 | 4/1994 | |
| GB | 2289674 | 11/1995 | |
| JP | 3007283 | 1/1991 | |
| JP | 5117238 | 5/1995 | |
| WO | 9006305 | 6/1990 | |
| WO | 9209579 | 6/1992 | |
| WO | 9322308 | 11/1993 | |

OTHER PUBLICATIONS

Uno, T., Takamatsu, M., Inoue, Y., Kawahata, Y., Iuchi, K., and Tsukamoto G., "Synthesis of Antimicrobial Agents. I. Syntheses and Antibacterial Activities of 7–(Azole Substituted)quinolones", Journal of Medicinal Chemistry, 30(12): 2163–2169 (Dec. 1987).
Research Disclosure, No. 291097, "Process for the manufacture of DNA–gyrase Inhibitors", (Jul. 1988).
Abstract, JP 05117238 (1993).
Abstract, JP 3007283 (1991).
Cram, Donald J., Hammond, George S., Organic Chemistry, McGraw–Hill Book Company, Second Edition, New York, N.Y., 1964, pp. 565–567.
Martel, A.M., et al., "Bay–12–8039", Drugs of the Future, 22:2, 109–113 (1997).

*Primary Examiner*—Patricia L. Morris

(57) ABSTRACT

The present invention relates to a novel process for preparing 8-methoxy-3-quinolonecarboxylic acids which are antibiotics having potent antibacterial action.

20 Claims, No Drawings

METHOD FOR PRODUCING 8-METHOXY-QUINOLINECARBOXYLIC ACIDS

This application is a continuation of U.S. Ser. No. 09/554,985, filed May 23, 2000, which is a 371 of PCT/EP98/07237 Nov. 12, 1998 now abandoned.

The invention relates to a process for preparing 8-methoxy-quinolonecarboxylic acids.

8-Methoxy-quinolonecarboxylic acids are antibiotics having potent antibacterial action against Gram-negative and Gram-positive bacteria. Thus, for example, the antibiotics 1-cyclopropyl-6-fluoro-1,4-dihydro-8-methoxy-7-(3-methyl-1-piperazinyl)-4-oxo-3-quinolinecarboxylic acid (INN: gatifloxacin, EP-A-230 295) and 1-cyclopropyl-7-[S,S]-2,8-diazabicyclo[4.3.0]non-8-yl)-6-fluoro-1,4-dihydro-8-methoxy-4-oxo-3-quinolonecarboxylic acid hydrochloride monohydrate (Bay 12-8039, EP-A-0 350 733) have a methoxy group in the 8-position.

Such highly potent antibacterial quinolonecarboxylic acids usually have a heteromonocyclic or heteropolycyclic amine radical in the 7-position of the quinolonecarboxylic acid. This cyclic amine radical is generally prepared by nucleophilic substitution of the corresponding 7-halogeno-quinolonecarboxylic acid with the respective amine. In principle, the 8-alkoxy group can be introduced before the introduction of the cyclic amine radical in the 7-position, or afterwards. Thus, EP-A-0 350 733 describes the preparation of the racemic betaine of the abovementioned Bay 12-8039, starting from the corresponding 8-methoxy compound whose preparation is described in EP-A-0 241 206 (Preparation 6), by nucleophilic substitution with the corresponding racemic amine. Analogously, the preparation of the enantiomerically pure betaine of Bay 12-8039 starting from the 8-methoxy compound by nucleophilic substitution with the enantiomerically pure amine is described in EP-A-0 550 903 (Example 19). However, the synthesis route described therein requires complicated isolation and purification by column chromatography which is undesirable for industrial scale. The latter approach is also used in EP-A-0 591 808 (Example Z 19).

Another way of introducing an 8-alkoxy substituent into the 7-amine-substituted quinolonecarboxylic acids consists in 8-alkoxy substitution after the cyclic amine substituent has been introduced into the 7-position of the corresponding 7,8-dihalogeno starting material.

Thus, EP-A-0 106 489 describes the route of 8-methoxy substitution after introduction of the heterocyclyl substituent in the 7-position by reaction of the corresponding 8-fluoro compound in methanol in the presence of potassium tertbutoxide. However, the reaction which is carried out in this publication with the 7-[2-[(methylamino)-methyl]-4-thiazole] compound requires 24 hours under reflux and is therefore unsuitable for a reaction on an industrial scale. Furthermore, it was observed that certain quinolonecarboxylic acids, such as, for example, the Bay 12-8039 described above, can not be prepared by this route since no reaction takes place under the conditions of the conversion under reflux for 24 hours.

EP-A-02 30 295 likewise describes the route of 8-alkoxy substitution starting from 8-halogeno-7-monocycloamine derivatives in methanol in the presence of alkali metal alkoxides. However, the reaction in the presence of sodium methoxide described in the examples of this publication requires very high temperatures of approximately 140 to 150° C. and very long reaction times, and the reaction is carried out in closed vessels under pressure. However, this process is not generally applicable for preparing 8-methoxy-quinolonecarboxylic acids. Thus, application of this process for preparing the above-described Bay 12-8039 does not lead to formation of end product even after 70 hours if the solvent used is MeOH.

If the reaction of the corresponding 8-fluoro compound with sodium methoxide is carried out in tetrahydrofuran, complete conversion requires very long reaction times (>24 h) and a large excess of methoxide.

In a similar manner, preparation of the 8-alkoxy derivatives in EP-A-0 235 762 is carried out by reacting the 8-halogeno-7-monocycloamine derivatives with alkali metal alkoxides. Furthermore, the preparation of 8-methoxy-quinolonecarboxylic acids by reacting the alkali metal alkoxides in solvents such as DMI (WO 93/22308, Chugai), with sodium methoxide in DMF or DMSO (EP-A-0 342 675, Chugai), with benzyl alcohol/sodium hydride (Research Disclosure No. 291 097, 1988), with sodium methoxide in DMF at 80° C. for 9 hours (JP 03007283 Yoshitomi), with methanol and a base (WO 90/06305, Dainippon), with NaH/trifluoroethanol in DMF (WO 92/09579), with sodium methoxide in methanol (JP-62 252772), with sodium methoxide/DMI at 80° C. (JP-05117 238, Chugai) and the reaction with sodium methoxide in methanol (J. Med. Chem. 30, 2163-2169) is described.

It is true that the reaction of the 8-halogen compounds with alkali metal alkoxides in polar aprotic solvents such as, for example, DMF generally leads to a virtually complete conversion if the alkali metal alkoxide is employed in excess. However, isolation of salts of the 8-alkoxy-quinolonecarboxylic acids from such solvents is complicated and virtually impossible to realize on an industrial scale.

It is therefore an object of the present invention to develop a process for preparing 8-methoxy derivatives of quinolonecarboxylic acids which permits short reaction times, operation under atmospheric pressure, complete conversion and easy work-up of the reaction mixture.

Surprisingly, it is possible to obtain 8-methoxy-quinolonecarboxylic acid derivatives in a process which meets the above conditions, by reacting the corresponding 8-halogeno-quinolonecarboxylic acid derivatives with ($C_1$–$C_3$)-alkanols or benzyl alcohol and sodium tert-butoxide or potassium tert-butoxide or sodium tert-amylate or potassium tert-amylate in the presence of aliphatic or cycloaliphatic ethers having 4 to 6 carbon atoms as solvent.

The invention, accordingly, provides a process for preparing compounds of the formula

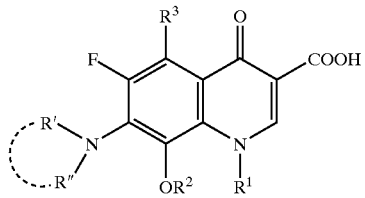

in which

R' and R" together with the linking nitrogen atom form a mono- or bicyclic heterocycle which may optionally contain in all ring moieties further nitrogen, oxygen or sulphur heteroatoms and which may optionally be substituted, in which $R^1$ represents $C_1$–$C_3$-alkyl, $FCH_2$—$CH_2$—, cyclopropyl, or represents phenyl or cyclopropyl, each of which is optionally mono- to trisubstituted by halogen, $R^2$ represents $C_1$–$C_3$-alkyl or benzyl,
$R^3$ represents H, halogen, $NH_2$, $CH_3$, characterized in that 8-halogeno-3-quinolonecarboxylic acid derivatives of the general formula

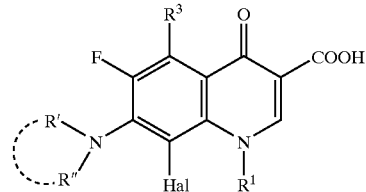

in which

Hal represents fluorine or chlorine and
$R^1$, $R^2$, $R^3$ and

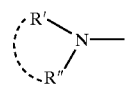

are each as defined above, are reacted in an aliphatic or cycloaliphatic ether having 4 to 6 carbon atoms as solvent in the presence of $C_1$–$C_3$-alkanols or benzyl alcohol with

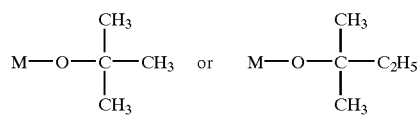

in which

M represents sodium or potassium.

The group

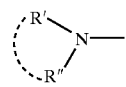

forms a mono- or bicyclic heterocycle which may optionally contain in all ring moieties further nitrogen, oxygen or sulphur hetero-atoms and which may optionally be substituted. The ring members R' and R" may represent identical or different ring components. Such mono- or bicyclic amine radicals in the 7-position of the quinolonecarboxylic acid skeleton are known in principle in the field of the quinolonecarboxylic acid antibiotics. By way of example, the patent publications EP-A-0 523 512, EP-A-0 230 295, EP-A-0 705 828, EP-A-0 589 318, EP-A-0 357 047, EP-A-0 588 166, GB-A-2 289 674, WO 92/09 579, JP-03-007 283, EP-A-0 241 206, EP-A-0 342 675, WO 93/22 308 and EP-A-0 350 733 may be mentioned.

Among these known amine radicals,

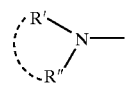

preferably represents

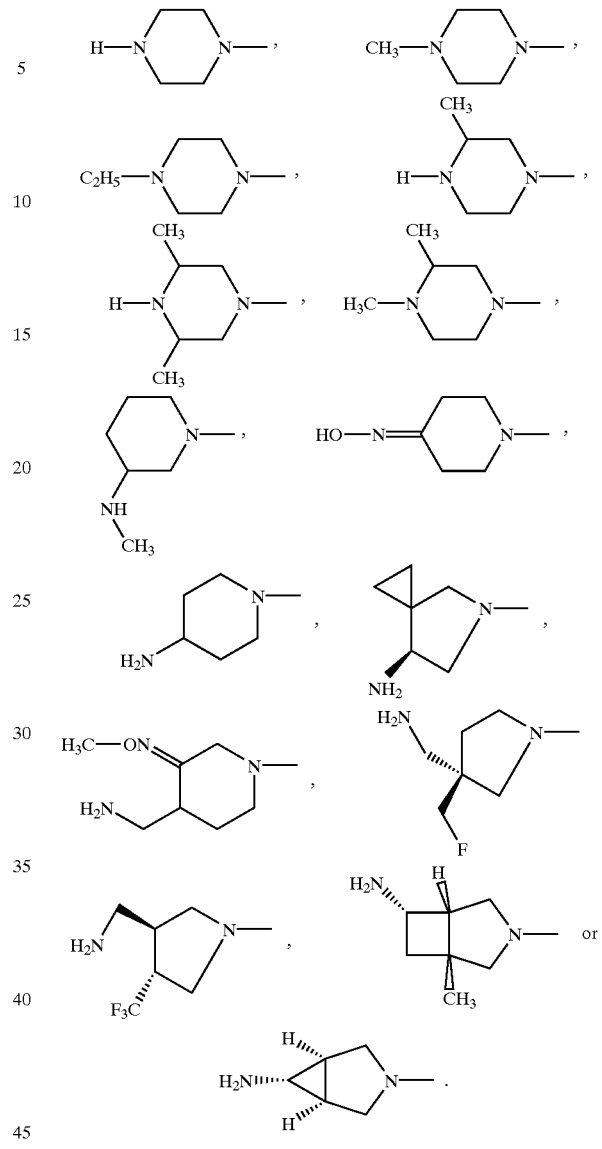

Very particularly preferably,

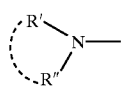

represents (a)

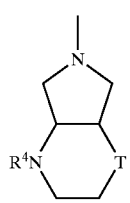

-continued (b) 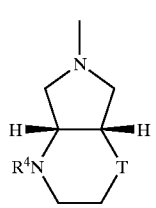

(c) 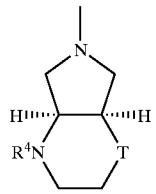

(d) 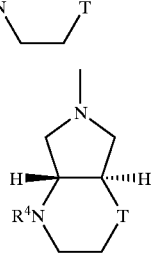

oder (e) 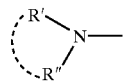

in which
T represents —O— or —CH$_2$— and
R$^4$ represents hydrogen, C$_1$–C$_3$-alkyl, C$_2$–C$_5$-oxoalkyl, —CH$_2$—CO—C$_6$H$_5$, —CH$_2$CH$_2$CO$_2$R$^5$,

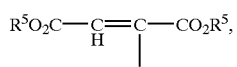

5-methyl-2-oxo-1,3-dioxol-4-yl-methyl, —CH=CH—CO$_2$R$^5$ or —CH$_2$CH$_2$—CN, in which
R$^5$ represents hydrogen or C$_1$–C$_3$-alkyl,
and the formula (a) includes any mixtures of the stereoisomers (b) to (e).
The amines corresponding to these definitions of are described in EP-A-0 550 903, and their reaction with the corresponding 6,7,8-trihalogeno-quinolonecarboxylic acids leads to the starting materials of the process according to the invention.

The aliphatic or cycloaliphatic ether having 4 to 6 carbon atoms is preferably selected from the group consisting of dimethoxyethane, dioxane and tetrahydrofuran.

Particularly high yields and short reaction times are achieved using tetrahydrofuran.

In the process according to the invention, Hal preferably represents fluorine.

The (C$_1$–C$_3$)-alkanol is preferably methanol, i.e. the process is preferably used for preparing the 8-methoxy compound.

M is preferably potassium, i.e. the reaction is preferably carried out using potassium tert-butoxide or potassium tert-amylate, particularly preferably using potassium tert-butoxide.

Based on 1 equivalent of the compound of the formula

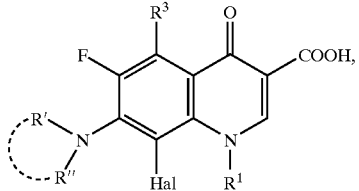

preferably 1 to 3, particularly preferably 1.1 to 1.3, equivalents of the (C$_1$–C$_3$)-alkanol or the benzyl alcohol, and 2 to 3, preferably 2.1 to 2.3, equivalents of the compound of the formula

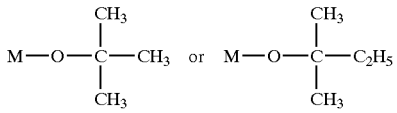

are employed.

The reaction is preferably carried out between 20° C. and the boiling point of the solvent at atmospheric pressure.

The process of the present invention is particularly suitable for preparing compounds of the formula

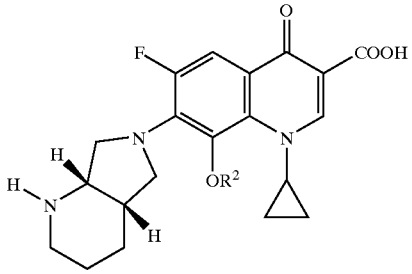

in which

R$^2$ represents C$_1$–C$_3$-alkyl or benzyl.

Here,

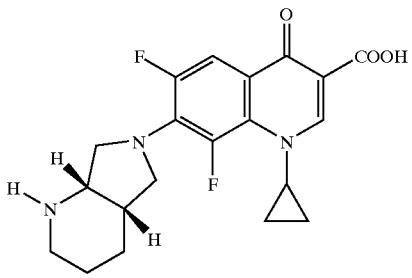

is preferably reacted in an aliphatic or cycloaliphatic ether having 4 to 6 carbon atoms as solvent in the presence of C$_1$–C$_3$-alcohols or benzyl alcohol with

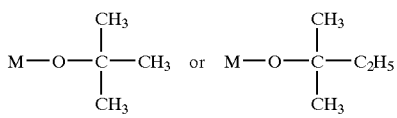

in which

M represents sodium or potassium.

The process is preferably carried out in dimethoxyethane, dioxane, tetrahydrofuran or mixtures of these.

Particularly preferably, the process is carried out in tetrahydrofuran as solvent.

The $(C_1-C_3)$-alkanol is preferably methanol, i.e. the 8-methoxy compound is prepared (Bay 12-8039).

M is preferably potassium.

Based on 1 equivalent of the compound of the formula

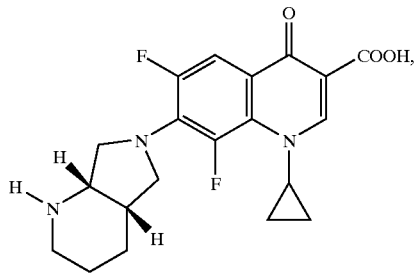

preferably 1 to 3, particularly preferably 1.1 to 1.3, equivalents of the $(C_1-C_3)$-alkanol or the benzyl alcohol, and 2 to 3, preferably 2.1 to 2.3, equivalents of the compound of the formula

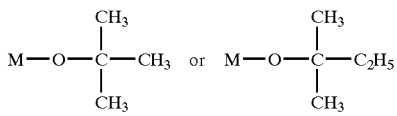

are employed.

The process is preferably carried out between 20° C. and the boiling point of the solvent at atmospheric pressure.

The process of the present invention is particularly suitable for preparing

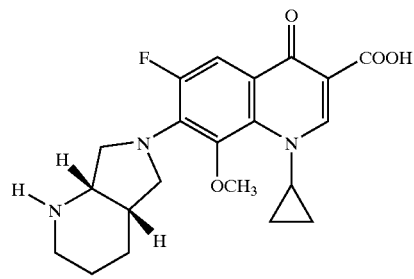

Bay 12-8039 (betaine form).

Here,

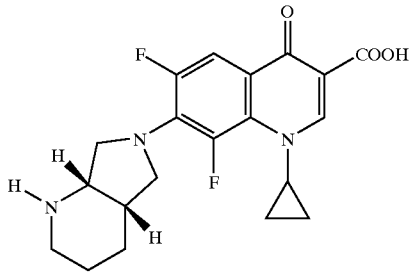

is reacted with methanol and preferably potassium tert-butoxide in tetrahydrofuran as solvent.

Based on one equivalent of the compound of the formula

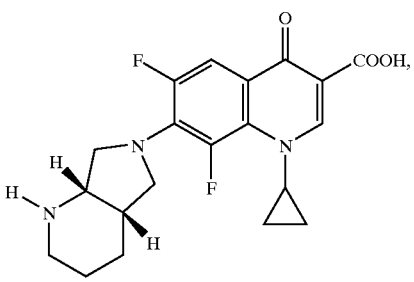

preferably 1 to 3, particularly preferably 1.1 to 1.3, equivalents of methanol and 2 to 3, preferably 2.1 to 2.3, equivalents of potassium tert-butoxide are employed, and the reaction is carried out between 20° C. and the boiling point of the solvent at atmospheric pressure.

A particular advantage of the process according to the invention consists in the fact that preparation of pharmaceutically acceptable salts, for example the hydrochlorides, of the above-described compounds succeeds in a particularly simple manner by admixing the resulting reaction mixture with dilute hydrochloric acid or by adding the reaction mixture to dilute hydrochloric acid and isolating the salt, preferably the hydrochloride, by filtration. This immediate preparation of the hydrochloride is preferably employed for preparing the compound of the following formula:

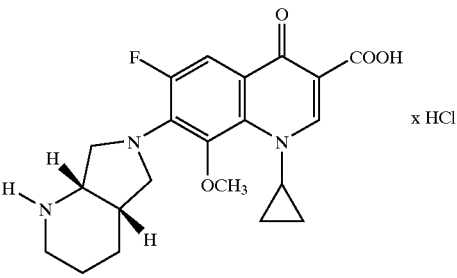

(Bay 12-8039, hydrochloride).

In a further aspect of the present invention, the compound described above (Bay 12-8039, hydrochloride) can surprisingly be isolated in high purity by recrystallization from water or a water/$(C_1-C_3)$-alkanol mixture. The purity of the compound obtained in this manner is already sufficient for many pharmaceutical applications. The recrystallization is preferably carried out from water or a water/ethanol mixture.

From the hydrochloride described above, it is furthermore surprisingly possible to obtain in a simple manner on industrial scale a particularly stable monohydrate of the formula

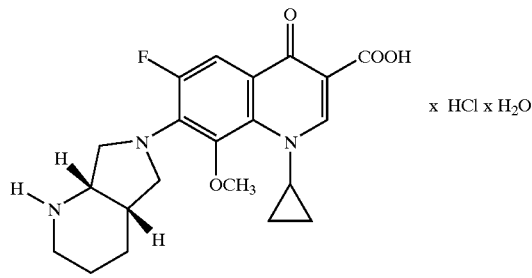

x HCl x H₂O having a particular crystal structure, as described in DE-A-1 95 46 249 (corresponds to EP-A-0 780 390), by drying the resulting product at from 40 to 60° C. and from 80 to 120 mbar. This drying is particularly preferably carried out at approximately 50° C. and approximately 100 mbar.

In the above definitions, ($C_1$–$C_3$)-alkyl or -alkyl radicals generally represent, for example, methyl, ethyl, propyl, isopropyl.

Particularly preferably, ($C_1$–$C_3$)-alkyl and the ($C_1$–$C_3$)-alkyl radical in the corresponding aliphatic radicals represents methyl.

EXAMPLE 1

Preparation of 1-cyclopropyl-7-([S,S]-2,8-diazabicyclo[4.3.0]non-8-yl)-6-fluoro-1,4-dihydro-8-methoxy-4-oxo-3-quinolonecarboxylic Acid Hydrochloride Using Potassium tert-butoxide
Quantities Employed:

| | | |
|---|---|---|
| 50.0 g | (0.129 mol) | 1-Cyclopropyl-7-([S,S]-2,8-diazabicyclo[4.3.0]non-8-yl)-6,8-difluoro-1,4-dihydroxy-4-oxo-3-quinolonecarboxylic acid (Bay z 7906) (prepared according to Example 1 of EP-A-0 550 903). |
| 270.0 ml | THF | |
| 6.2 ml | (0.155 mol) | Methanol |
| 159.1 g | (0.284 mol) | Potassium tert-butoxide solution (20% strength in THF) |
| 128 ml | Water | |
| 38 ml | Hydrochloric acid, conc. | |
| 30 ml | Water | |
| 60 ml | Ethanol | |
| 110 ml | Ethanol | |
| 330 ml | Water | |
| 3 × 15 ml | Ethanol | |

Procedure:

Under nitrogen, 50.0 g of Bay z 7906 in 270 ml of THF and 6.2 ml of methanol were initially charged in a 1000 ml three-necked flask fitted with stirrer and thermometer. The mixture is heated and, from approximately 60° C. onwards, 80 ml of a potassium tert-butoxide solution (20% strength in THF), corresponding to 1 equivalent, is added over a period of approximately 5 min. A yellow suspension results, which slowly becomes more viscose and which is finally white. The mixture is stirred under reflux for 15 min. The suspension does not change. Under reflux, the remaining potassium tert-butoxide solution is added over a period of 5 min. The mixture is stirred at reflux for 2.5 hours and subsequently cooled to room temperature.

To precipitate the hydrochloride, 128 ml of water and 38 ml of conc. hydrochloric acid are initially charged in a double-jacket flask fitted with stirrer, revolution counter and thermostat. With cooling and at 500 rpm, the reaction solution obtained above is added dropwise over a period of 2 hours at approximately 20 to 22° C. After the addition of approximately 50 ml, the mixture is seeded with-12.5 mg of Bay 12-8039. After the addition is complete, the mixture is stirred at 8° C. for approximately 30 min. A solution forms. The mixture is filtered and the filter cake is washed first with 30 ml of water and then with 60 ml of ethanol. The precipitated end product can be filtered very easily and is dried at 50° C. under reduced pressure.

This gives 47.1 g of the product.

Purification and Monohydrate Formation

For purification, 46.6 g of the precipitated product are dissolved under reflux in 110 ml of ethanol/330 ml of water, and the mixture is allowed to cool to 20 to 22° C. over a period of 2 hours. At approximately 50° C., the mixture is seeded with 12.5 mg of Bay 12-8039. The seed crystals do not dissolve. The mixture is stirred at 20 to 22° C. for a further hour and filtered, and the filter cake is washed with 3×15 ml of ethanol. Drying at approximately 50° C. and a pressure of 100 mbar results in the defined formation of the monohydrate of Bay 12-8039 hydrochloride.

This gives 31.9 g of yellow crystals of a purity which is sufficient for many pharmacological applications.

EXAMPLE 2

Preparation of 1-cyclopropyl-7-([S,S]-2,8-diazabicyclo[4.3.0]non-8-yl)-6-fluoro-1,4-dihydro-8-methoxy-4-oxo-3-quinolonecarboxylic Acid Hydrochloride Using Potassium tert-amylate Quantities Employed:

| | | |
|---|---|---|
| 10.0 g | (25.7 mmol) | Bay z 7906, Pt. 501781 |
| 54 ml | THF | |
| 1.24 ml | (30, 8 mmol) | Methanol |
| 35.6 g | (56, 5 mmol) | Potassium tert-amylate solution (20% strength in THF) |
| 26.6 ml | | Water |
| 7.6 ml | | Hydrochloric acid, conc. |
| 6.0 ml | | Water |
| 12.0 ml | | Ethanol |

Procedure:

10 g of Bay z 7906 are initially charged in 54 ml of THF and 1.24 ml of methanol. The mixture is heated, and 17 ml of potassium tert-amylate solution (20% strength in THF), corresponding to 1 equivalent, are added from 60° C. onwards over a period of approximately 5 minutes. The mixture is then stirred under reflux for 30 minutes. Under reflux, the remaining potassium tert-amylate solution is added over a period of 5 minutes. The mixture is stirred at reflux for 2.5 hours and subsequently cooled to room temperature. To precipitate the hydrochloride, 26.6 ml of water and 7.6 ml of hydrochloric acid (conc.) are initially charged. At 500 rpm and with cooling, the reaction solution is added dropwise over a period of 2 hours at approximately 20 to 22° C. After addition of approximately 9 ml, the mixture is seeded with Bay 12-8039. After the addition is complete, the mixture is stirred at 8° C. for 30 minutes. A suspension is formed. The suspension is filtered and the filter cake is washed first with 6 ml of water and then with 12 ml of ethanol and dried under reduced pressure at 50° C. This gives 8.6 g.

The product can be purified and converted into the monohydrate using the procedure of Example 1.

Comparative Example
(Reaction of Bay z 7906 in THF with Sodium Methoxide)
Amounts Employed:

| | | |
|---|---|---|
| 50.0 g | (0.129 mol) | Bay z 7906 |
| 1040 ml | | THF |
| 116.1 g | (0.645 mol) | Sodium methoxide solution (30% strength in methanol) |
| 49 ml | | Hydrochloric acid, conc. |
| 77 ml | | THF |
| 38 ml | | Water |
| 385 ml | | Water |
| 2 × 38 ml | | Water |
| 297 ml | | Methanol |
| 2 × 10 ml | | Methanol |
| 68 ml | | Ethanol |
| 34 ml | | Water |
| 2 × 10 ml | | Ethanol |

Procedure:

In a 2000 ml three-necked flask fitted with stirrer and thermometer, 50.0 g of Bay z 7906 in 1040 ml of THF and 116.1 g of sodium methoxide solution (30% strength in methanol) are initially charged under nitrogen. With stirring, the mixture is heated to reflux and the progress of the reaction is monitored by HPLC.
(Bay z 7906 [Starting Material] Content:

after 6 h RF=56.5%;
after 30 h RF=11.7%;
after 70 h RF=1.4%).

After 70 hours of stirring under reflux, the mixture is cooled to 10 to 15° C. and adjusted to pH 6.8 to. 7.0 using conc. hydrochloric acid (consumption of conc. hydrochloric acid 48 ml). The precipitate is filtered off with suction and washed first with 77 ml of THF and then with 38 ml of water.

The moist solid (108.2 g) is suspended in 385 ml of water, stirred at 20 to 25° C. for 30 minutes, filtered off with suction and washed twice with 38 ml of water (poor filtration properties).

The solid is dried under reduced pressure at 50° C. (40.4 g) and dissolved at reflux in 297 ml of methanol.

After cooling to approximately 10° C., the precipitated crystals are filtered off with suction and washed twice with 10 ml of methanol each time.

The solid is dried under reduced pressure at 50° C. (21.1 g) and dissolved under reflux in 68 ml of ethanol and 34 ml of water. After cooling to 20 to 25° C., the mixture is stirred for one hour and the precipitated crystals are filtered off with suction and washed twice with 10 ml of ethanol. Drying under reduced pressure at 50° C. gives 16.2 g of orange crystals.

Comparison between the examples according to the invention and the comparative example shows that, even after a reaction time of 70 h, the reaction with sodium methoxide in THF gives a lower yield.

The process according to the invention thus offers, in particular on an industrial scale, enormous advantages in terms of yield, reaction time and work-up.

What is claimed is:
1. Process for preparing 3-quinolonecarboxylic acid derivatives of the general formula

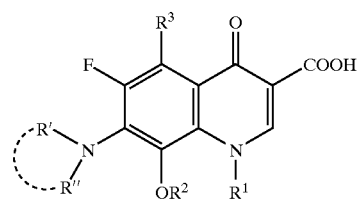

wherein

R' and R" together with the linking nitrogen atom form a mono- or bicyclic heterocycle which may optionally contain in all ring moieties further nitrogen, oxygen or sulphur heteroatoms and which may optionally be substituted, wherein $R^1$ represents $C_1$–$C_3$-alkyl, $FCH_2$—$CH_2$—, cyclopropyl, or represents phenyl or cyclopropyl, each of which is optionally mono- to trisubstituted by halogen, $R^2$ represents $C_1$–$C_3$-alkyl or benzyl, $R^3$ represents H, halogen, $NH_2$, $CH_3$, comprising reacting 8-halogeno-3-quinolonecarboxylic acid derivatives of the general formula

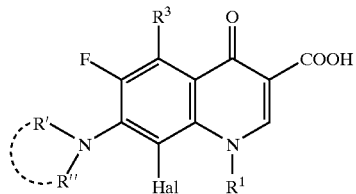

wherein
Hal represents fluorine or chlorine and $R^1$, $R^2$, $R^3$ and

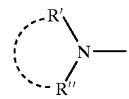

are each as defined above,
in an aliphatic or cycloaliphatic ether having 4 to 6 carbon atoms as solvent in the presence of $C_1$–$C_3$-alkanols or benzyl alcohol with

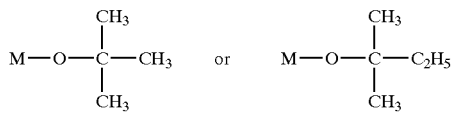

wherein
M represents sodium or potassium.

2. The process according to claim 1, wherein the solvent selected is selected from the group consisting of dimethoxyethane, dioxane and tetrahydrofuran.

3. The process according to claim 2, wherein the solvent is tetrahydrofuran.

4. The process according to claim 1, wherein Hal represents fluorine.

5. The process according to claim 1, wherein the ($C_1$–$C_3$)-alkanol is methanol.

6. The process according to claim 1, wherein M is potassium.

7. The process according to claim 1, wherein based on 1 equivalent of the compound of the formula

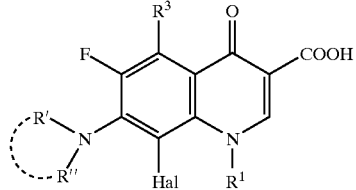

1 to 3 equivalents of the ($C_1$–$C_3$)-alkanol or the benzyl alcohol, and 2 to 3 equivalents of the compound of the formula

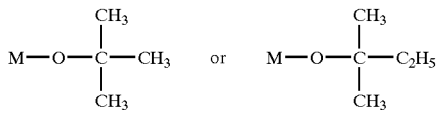

are employed.

8. The process according to claim 1, characterized in that the reaction is carried out between 20° C. and the boiling point of the solvent at atmospheric pressure.

9. The process according to claim 1, wherein

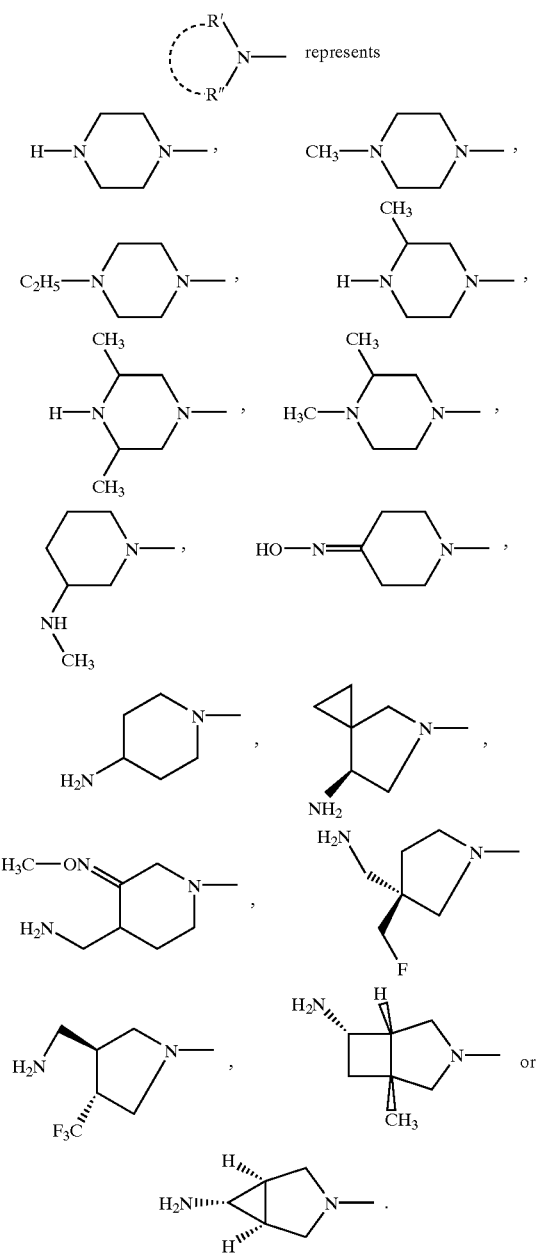

10. The process according to claim 1, wherein

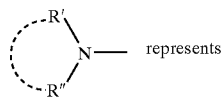

represents (a)

-continued (b) 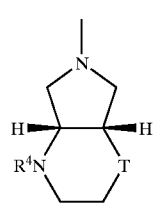

(c) 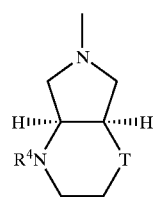

(d) 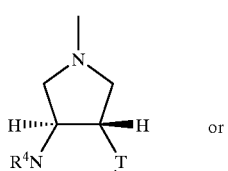 or (e) 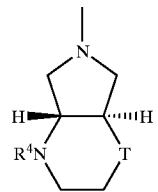

wherein
T represents —O— or —CH$_2$— and
R$^4$ represents hydrogen, C$_1$–C$_3$-alkyl, C$_2$–C$_5$-oxoalkyl, —CH$_2$—CO—C$_6$H$_5$, —CH$_2$CH$_2$CO$_2$R$^5$,

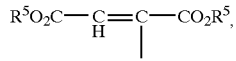

5-methyl-2-oxo-1,3-dioxol-4-yl-methyl, —CH=CH—CO$_2$R$^5$ or
—CH$_2$CH$_2$—CN,
wherein
R$^5$ represents hydrogen or C$_1$–C$_3$-alkyl,
and the formula (a) includes any mixtures of the stereoisomers (b) to (e).

11. Process for preparing

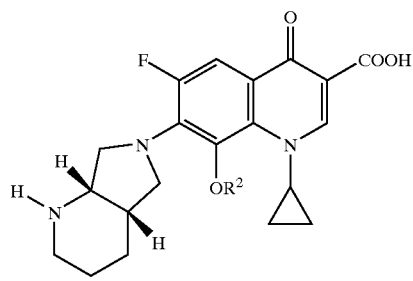

in which
R$^2$ represents C$_1$–C$_3$-alkyl or benzyl,
comprising reacting

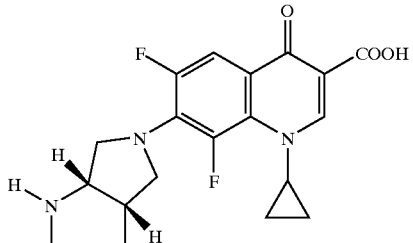

is reacted in an aliphatic or cycloaliphatic ether having 4 to 6 carbon atoms as solvent in the presence of C$_1$–C$_3$-alcohols or benzyl alcohol with

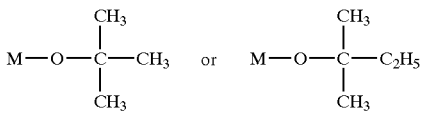

wherein
M represents sodium or potassium.

12. The process according to claim 11, wherein the solvent is selected from the group consisting of dimethoxyethane, dioxane and tetrahydrofuran.

13. The process according to claim 12, wherein the solvent is tetrahydrofuran.

14. The process according to claim 11, wherein the (C$_1$–C$_3$)-alkanol is methanol.

15. The process according to claim 11, wherein M is potassium.

16. The process according to claim 11, wherein, based on 1 equivalent of the compound of the formula

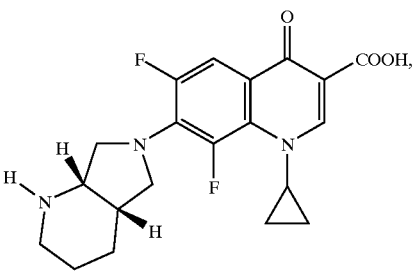

1 to 3 equivalents of the (C$_1$–C$_3$)-alkanol or the benzyl alcohol, and 2 to 3 equivalents of the compound of the formula

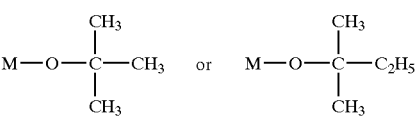

are employed.

17. The process according to claim 11, wherein the reaction is carried out between 20° C. and the boiling point of the solvent at atmospheric pressure.

18. The process according to claim 11 for preparing

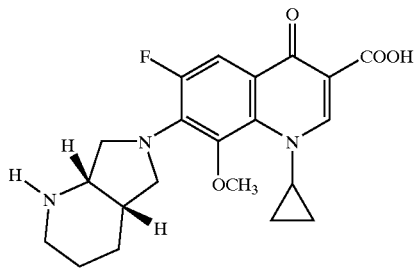

further comprising reacting

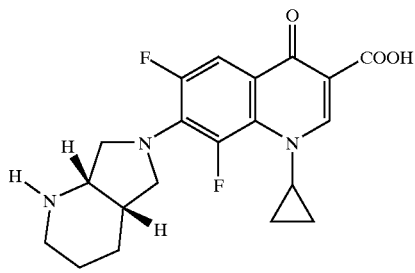

methanol and potassium tert-butoxide in tetrahydrofuran as solvent.

19. The process according to claim 18, wherein, based on one equivalent of the compound of the formula

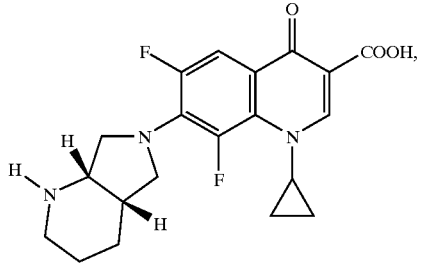

1 to 3 equivalents of methanol and 2 to 3 equivalents of potassium tert-butoxide are employed.

20. The process according to claim 18, wherein the reaction is carried out between 20° C. and the boiling point of the solvent at atmospheric pressure.

* * * * *